United States Patent [19]

Bickel

[11] 4,345,475
[45] Aug. 24, 1982

[54] METHOD AND APPARATUS FOR RECEIVING ULTRASONIC ENERGY BY OPTICAL MEANS

[75] Inventor: Wolf Bickel, Bergisch Gladbach, Fed. Rep. of Germany

[73] Assignee: Krautkramer-Branson, Inc., Stratford, Conn.

[21] Appl. No.: 205,304

[22] Filed: Nov. 10, 1980

[30] Foreign Application Priority Data

Jan. 25, 1980 [DE] Fed. Rep. of Germany ....... 3002620

[51] Int. Cl.³ .......................................... G01N 29/00
[52] U.S. Cl. ........................................ 73/657; 73/655
[58] Field of Search ................................... 73/657, 655

[56] References Cited

U.S. PATENT DOCUMENTS 4,129,041 12/1978 Bickel ...................................... 73/657

*Primary Examiner*—Anthony V. Ciarlante
*Attorney, Agent, or Firm*—Ervin B. Steinberg; Philip J. Feig

[57] ABSTRACT

When sensing the presence of ultrasonic energy in a workpiece portion by illuminating such portion with light from a single-mode frequency stabilized laser, the reflected light, frequency modulated by the Doppler effect due to the ultrasonic energy induced deflection of the workpiece portion, is passed through a gas filled light filter. The frequency modulated light is amplitude modulated by the filter by selecting the frequency of the laser to cause a point of operation which is located along a steep slope portion of the absorption curve characteristic of the filter. To increase the steepness of the slope portion of the filter, the present invention discloses the use of laser light to saturate the filter in a part region.

8 Claims, 6 Drawing Figures

METHOD AND APPARATUS FOR RECEIVING ULTRASONIC ENERGY BY OPTICAL MEANS

SUMMARY OF THE INVENTION

This invention relates to an ultrasonic test method utilizing the optical reception of ultrasonic waves by illuminating a workpiece surface which is physically in phase with the ultrasonic wave. Illumination of the workpiece surface is accomplished by light from a frequency stabilized single-mode laser. The light, which is reflected at a surface portion of the workpiece and which is frequency modulated by the Doppler effect due to the ultrasonic wave, is then passed through a light filter. The frequency of the laser is selected in such a manner that an amplitude modulation of the reflected light is effected along the slope of the light filter absorption curve. The amplitude modulated light is then transmitted to a photoelectric means which produces an electrical signal which is a function of the ultrasonic wave intensity in the illuminated workpiece portion.

As has been disclosed previously in U.S. Pat. No. 4,129,041 issued to W. Bickel and dated Dec. 12, 1978 it is possible to pass light, which has been reflected at a surface portion of a workpiece and which has been frequency modulated by the Doppler effect on account of sonic energy propagated in the workpiece, through a light filter and to select the frequency of the laser in such a way that an amplitude modulation is effected along the slope of the light filter absorption curve, and to transmit, subsequently, the amplitude modulated light to photoelectric means to generate a signal which is a function of the ultrasonic intensity. The surface of the workpiece is illuminated with laser light for the purpose of sensing the ultrasonic energy. The surface elements of the workpiece move under the influence of the ultrasonic pressure field which is present in the workpiece and at a velocity which is termed particle velocity. By virtue of the physical deflection of the workpiece surface the reflected laser light is frequency modulated as a result of the Doppler effect. A light filter is used as a slope discriminator for producing an amplitude modulation of the reflected laser light which has been frequency-modulated by the Doppler effect, see U.S. Pat. No. 4,129,041 supra which is incorporated in this disclosure by reference. The steepness of the absorption curve slope of the light filter is determinant of the degree of amplitude modulation. Gas-filled absorption cells which, according to the state of the art, contain gases under a low pressure are used as the light filters. Thus, for example, in the case of a laser light having a wavelength of 514.5 nm, a gas suitable for the absorption cell is the vapor of iodine $^{127}I_2$ or that of the iodine isotope $^{129}I_2$ under low pressure. A disadvantage is that this gas at room temperature has an absorption region with a band width of the order of magnitude of 1 GHz in the vicinity of the stated wavelength. To obtain an amplitude modulation of about one percent, that is, a fluctuation in the intensity of the light of the order of magnitude of one percent, the frequency shift in the received laser light would have to be of the order of magnitude of 10 MHz. However, the frequency modulation of the reflected and received laser light, due to the Doppler effect caused by the vibrations of the surface portions of the workpiece under the action of the ultrasonic pressure wave, is substantially lower at the frequencies and ultrasonic intensities used for testing of materials. Hence, only low level amplitude modulations are obtained.

It is a principal object of the present invention to substantially increase the amplitude modulation achievable for a given frequency shift by increasing the steepness of the slope of the light filter blocking characteristic in the absorption region.

The broad absorption line of a gas filled absorption cell is thermodynamically determined by the temperature which is necessary for maintaining the gaseous state, that is to say, by the kinetic energy of the atoms and molecules. However, if a gas-filled absorption cell of this type is irradiated in its relatively broad absorption range with very narrow-band laser light of adequate intensity, a saturation phenomenon is produced in the absorption cell for the narrow frequency region of the laser light. Hence, the absorption characteristic of the filter is largely cancelled within this narrow-band region.

When absorbing photons, atoms or molecules of the illuminated gas volume are excited per unit of time. The more atoms or molecules is excited, the fewer are available for further absorption. If by far the greater part of the atoms or molecules are excited by a very intense illumination of the gas volume with a corresponding frequency, the absorption ability for another light beam having the same frequency is largely cancelled. Thus, the gas-filled absorption cell becomes transparent for these light frequencies. This consideration applies only to the atoms and molecules which have an appropriate velocity component in the direction of the incident light. The remaining atoms and molecules, with their kinetic energy corresponding to the temperature, do not participate in this saturation process. This means that the saturated region is a very narrow frequency band compared with the absorption region. This is indicated in FIG. 2.

DETAILED DESCRIPTION OF THE INVENTION

As shown in the referenced patent, it is advantageous to place the operating point of the slope discriminator along one of the steep slopes of the saturated region of the light filter absorption curve.

Figure 2:
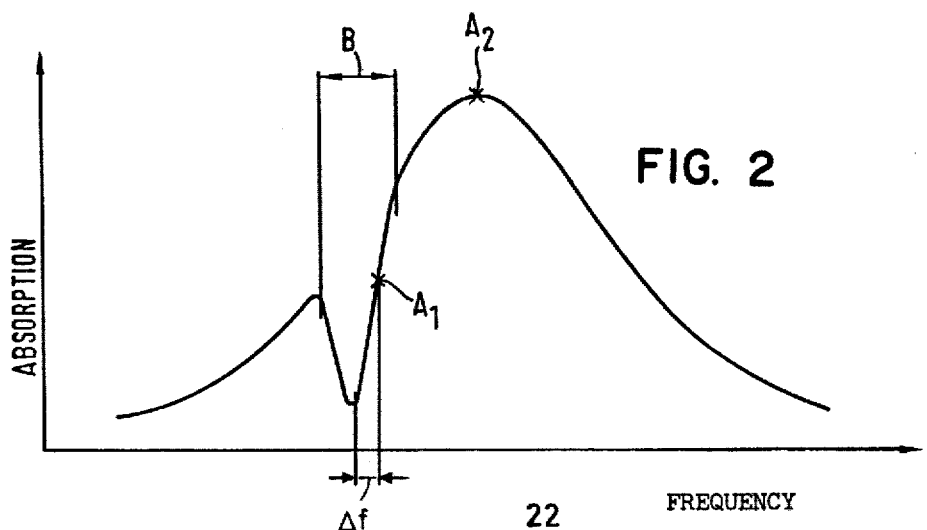
FIG. 2 shows an absorption curve (blocking characteristic) of a light filter with a saturated part region.
Figure 3:
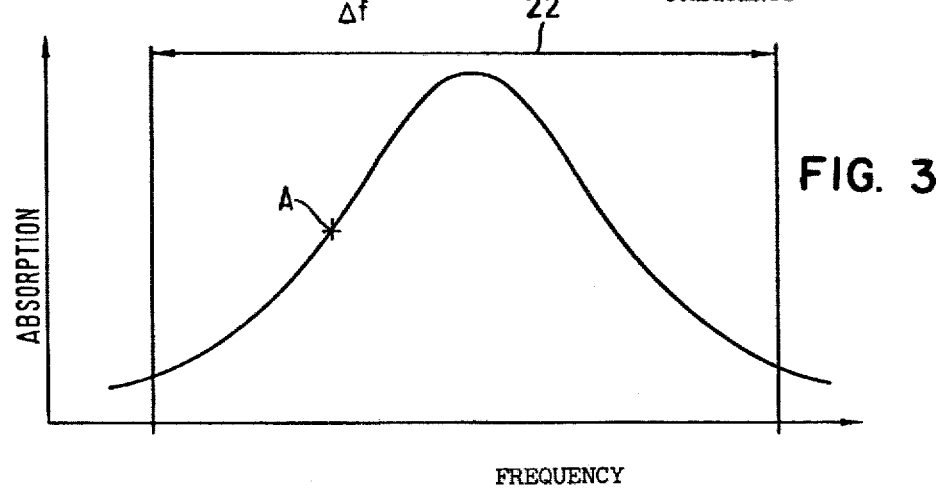
FIG. 3 shows an absorption curve of a light filter according to the state of the art, that is, no saturated part region.

In FIG. 2, the point $A_1$ along the light filter absorption curve is such an operating point. Therefore, for the same frequency shift of the light, the amplitude modulation of the light obtained is greater than that at an operating point A of FIG. 3 representing a light absorption cell which is not saturated in the part region.

Figure 1:
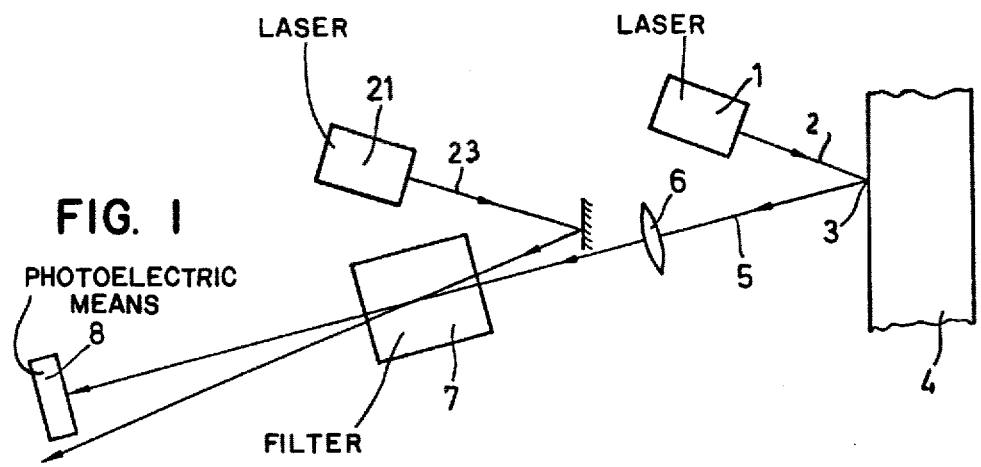
FIG. 1 is a schematic embodiment of the present invention.

In the illustrative embodiment according to FIG. 1, a frequency stabilized single-mode laser 1 illuminates the surface portion 3 of a workpiece 4 with a light beam 2. The reflected light beam 5 is frequency-modulated by the Doppler effect due to the ultrasonic vibration manifest at the workpiece surface 3. A collector lens 6 focuses the laser light 5 reflected at the surface portion 3 and passes the light via the light filter 7 to the photoelectric means 8. The likewise frequency stabilized single-mode laser 21, with its high-intensity light beam, illuminates the light filter 7, if appropriate via deflection mirror means, so that the light filter 7 is saturated in part regions of its absorption curve and its absorption ability in these part regions is thus strongly diminished. Such a saturated frequency region B is shown in FIG. 2. This arrangement makes very stringent demands on the frequency stability of the lasers.

Figure 4:
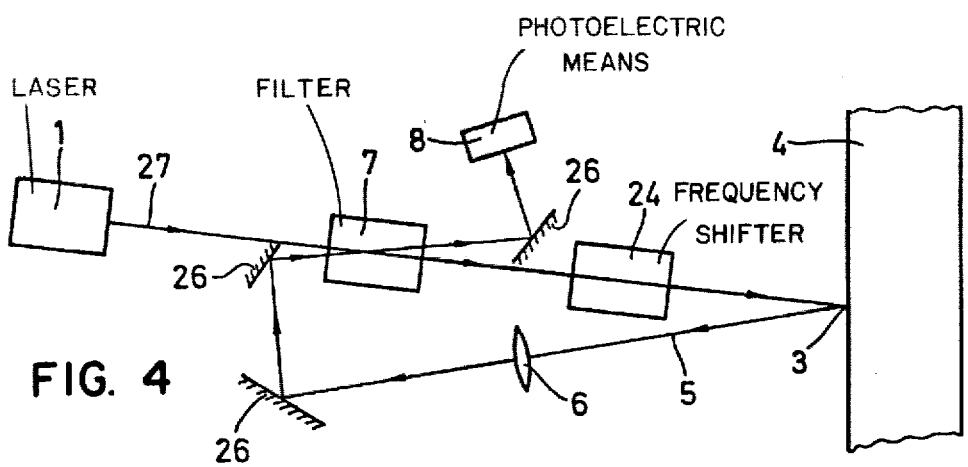
FIG. 4 shows, by way of example, an arrangement for carrying out the present invention with a single laser.

Advantageously, the laser 1 which illuminates the surface of the workpiece and which must be sufficiently frequency-stabilized, can also be used for saturating the light filter 7. Such an arrangement is shown in FIG. 4. The light beam 27 (FIG. 4) of the frequency stabilized single-mode laser 1 is passed through the light filter 7 which can comprise an absorption cell filled with iodine vapor under low pressure. In the region B of its absorption region 22, (FIG. 2), the light filter becomes transparent because of the above described saturation phenomenon. With adequate laser power and a suitable density of the iodine vapor, which density is adjustable via the temperature of the gas, a large part of the light beam re-emerges from the absorption cell, undergoes a constant frequency shift $\Delta f$ in the frequency shifter 24 and illuminates the surface 3 of the workpiece 4. The reflected light 5, which has been frequency modulated by the Doppler effect due to the acoustic energy responsive motion, is passed through the collection optics 5 and a deflection mirror arrangement 26 and, as far as possible, in the same direction as the saturating light beam 27, through the light filter 7. An electrical value, for example an electric voltage which depends on the light intensity, is generated by a photoelectric means 8 which receives the light after passage through the filter 7. The frequency shift $\Delta f$ is selected such that the operating point of the slope discriminator formed by the light filter is positioned along the steepest portion of the saturation slope, such as point $A_1$. Because of the constant frequency shift $\Delta f$, this operating point is maintained. This applies even if the frequency of the laser drifts. The only precondition is that the laser frequency remains within the absorption line of the filter, which condition is assured by the frequency stabilization of the laser. The frequency shifter 24 can be formed, for example, from Bragg cells, from oscillating mirrors, or from other means as known in the art. The gas used for the absorption cell of the light filter can be, as previously mentioned, vapor of the iodine isotope $^{129}I_2$ or $^{127}I_2$.

In a simplified version of the present embodiment, the frequency shifter 24 can be omitted. The frequency shift $\Delta f$ is then zero. This means that the frequency of the received light and that of the saturating light are equal, and the result of this is an operating point along the peak of the saturation curve. Any change of the frequency of the received light then also leads to an amplitude modulation, but with a rectifier effect and a smaller amplitude.

Figure 5:
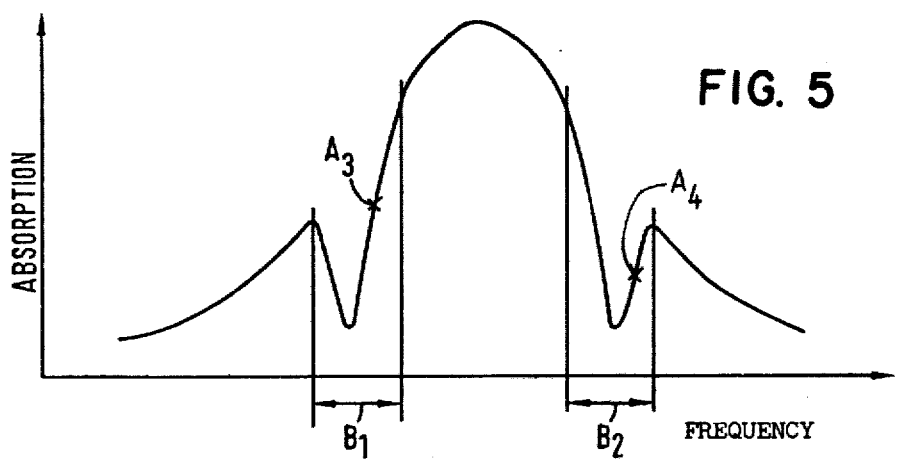
FIG. 5 shows an absorption curve for a light filter built into the resonating cavity of the laser.
Figure 6:
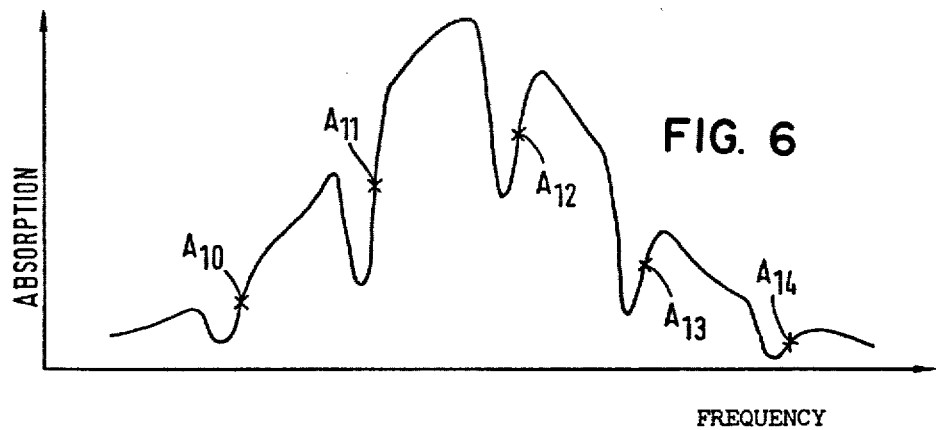
FIG. 6 shows an absorption curve for a light filter, taking into account the hyperfine structure.

In a modification of the above embodiment, the absorption cell 7 can be arranged within the resonant cavity of the laser used for saturation. The very high light intensity prevailing in the resonant cavity of the laser is thus utilized for saturation. However, since a respective light wave passes back and forth between the mirrors of the resonating cavity, two saturation regions are formed which are symmetrical with respect to the center of the absorption line and which coincide only if the laser is tuned to the center of the line. This is indicated in FIG. 5 by the regions $B_1$ and $B_2$ with the respective operating points $A_3$ and $A_4$. If several saturation lines are produced by the hyperfine structure in the gas of the absorption cell, as shown in FIG. 6, several operating points $A_{10}$, $A_{11}$, $A_{12}$ and so on result, corresponding to the frequency shift $\Delta f$.

If the saturating laser operates with more than only one frequency, all of the laser frequencies falling within the absorption region of the light filter contribute with their saturation regions to the amplitude modulation, that is to say, to the formation of the electrical signal.

By means of the narrow-band saturation obtained with the aid of a frequency stabilized single-mode laser, a narrow-band saturation region can be produced in a light filter comprising an absorption cell to cause thereby a very steep slope which, in turn, results in a higher degree of amplitude modulation of light than that obtained by the much shallower slopes of a non-saturated absorption cell.

What is claimed is:

1. The method of optical reception of ultrasonic energy in testing of workpieces by ultrasonic energy wherein a surface portion of such workpiece is illuminated by the light from a frequency stabilized single-mode laser, the laser light reflected at said surface portion is frequency modulated by the Doppler effect responsive to ultrasonic energy deforming said workpiece portion and is passed through a gas filled light filter, the frequency of said single-mode laser being selected to cause an amplitude modulation of said reflected light along the slope of the absorption curve of said filter, and the amplitude modulated light passed through said filter is transmitted to a photoelectric means to produce an electrical signal which is responsive to the intensity of the ultrasonic energy at said workpiece surface portion, the improvement comprising:

illuminating said workpiece portion (3) with a first laser light beam (2);
   irradiating the gas in the light filter (7) with a second laser light beam (23) of such intensity that the filter (7) substantially loses its absorption ability for the frequency or frequencies of said second laser light beam (23) to cause in the original absorption region (22) of said filter (7) at least one part region (B) characterized by a steeper slope of the absorption curve.

2. The method of optical reception of ultrasonic energy as set forth in claim 1, irradiating said light filter (7) with light (27) from the laser (1) which illuminates the workpiece portion (3).

3. The method of optical reception of ultrasonic energy as set forth in claim 2, said light filter (7) being disposed in the resonant cavity of said laser (1) which illuminates the workpiece portion (3).

4. An apparatus for sensing an ultrasonic wave from a workpiece surface portion by optical means free of physical contact with such workpiece portion comprising:

a frequency stabilized single mode laser disposed for transmitting a beam of coherent light upon the workpiece surface portion undergoing deformation responsive to the presence of an ultrasonic wave which causes the light to become frequency modulated by the Doppler effect;

a gas filled light filter;

means disposed for receiving the frequency modulated light reflected at said surface portion and transmitting said reflected light through said filter, the frequency of said laser and that of said filter being selected to cause the nominal frequency of said laser to be disposed along the steep portion of the slope of the light absorption line of said filter whereby to provide amplitude modulated light passed through said filter;

means for irradiating said filter with laser light of the same or shifted frequency as the light transmitted upon the workpiece surface portion for causing said filter to substantially lose its absorption characteristic in the original region and exhibit a part region with steeper slopes, and photoelectric means disposed for receiving the amplitude modulated light passed through said filter and providing an electrical signal responsive to the light transmitted through said filter and, hence, a measure of said deformation.

5. An apparatus for sensing an ultrasonic wave as set forth in claim 4, said means for irradiating said filter comprising a second frequency stabilized single mode laser.

6. An ultrasonic apparatus for sensing an ultrasonic wave as set forth in claim 4, said means for irradiating said filter and said stabilized laser disposed for transmitting a beam of light upon the workpiece surface portion being the same laser.

7. An ultrasonic apparatus for sensing an ultrasonic wave as set forth in claim 6, said filter being disposed in the resonant cavity of said single laser.

8. An ultrasonic apparatus as described in claim 4, said light being passed through said filter from said workpiece to said photoelectric means and said light causing said filter to lose substantially its absorption characteristic passing through said filter in substantially the same direction.

* * * * *